(12) United States Patent
Filimonov et al.

(10) Patent No.: US 12,702,317 B2
(45) Date of Patent: Aug. 11, 2026

(54) METHOD AND SYSTEM FOR HEART RATE EXTRACTION FROM RGB IMAGES

(71) Applicant: Harman Becker Automotive Systems GmbH, Karlsbad-Ittersbach (DE)

(72) Inventors: Andrey Viktorovich Filimonov, Kamenki (RU); Ivan Sergeevich Shishalov, Nizhniy Novgorod (RU); Roman Aleksandrovich Ershov, Nizhny Novgorod (RU); Andrey Sergeevich Shilov, Nizhny Novgorod (RU)

(73) Assignee: HARMAN BECKER AUTOMOTIVE SYSTEMS GMBH, Karlsbad-Ittersbach (DE)

( * ) Notice: Subject to any disclaimer, the term of this patent is extended or adjusted under 35 U.S.C. 154(b) by 8 days.

(21) Appl. No.: 18/550,913

(22) PCT Filed: Mar. 30, 2021

(86) PCT No.: PCT/RU2021/000135
§ 371 (c)(1),
(2) Date: Sep. 15, 2023

(87) PCT Pub. No.: WO2022/211656
PCT Pub. Date: Oct. 6, 2022

(65) Prior Publication Data

US 2024/0138692 A1 May 2, 2024

(51) Int. Cl.

| | |
|---|---|
| ***A61B 5/024*** | (2006.01) |
| ***A61B 5/00*** | (2006.01) |
| ***A61B 5/103*** | (2006.01) |

(52) U.S. Cl.
CPC ........ *A61B 5/02427* (2013.01); *A61B 5/0077* (2013.01); *A61B 5/1032* (2013.01); *A61B 5/6893* (2013.01)

(58) Field of Classification Search
CPC ....... A61B 5/0077; A61B 5/02; A61B 5/0205; A61B 5/024; A61B 5/02416; A61B 5/026; A61B 5/0261
See application file for complete search history.

(56) References Cited

U.S. PATENT DOCUMENTS

| | | | |
|---|---|---|---|
| 8,977,347 | B2 | 3/2015 | Mestha et al. |
| 9,642,536 | B2 | 5/2017 | Kashef et al. |

(Continued)

FOREIGN PATENT DOCUMENTS

| | | | |
|---|---|---|---|
| JP | H1189807 | A | 4/1999 |
| JP | 2014198202 | A | 10/2014 |

(Continued)

OTHER PUBLICATIONS

Japanese Patent Office, Office Action Issued in Application No. 2023-555268, Nov. 21, 2024, 12 pages.

(Continued)

*Primary Examiner* — Carolyn A Pehlke
(74) *Attorney, Agent, or Firm* — McCoy Russell LLP

(57) ABSTRACT

Method and system for determining one or more heart beat features using remote photoplethysmography (rPPG). The method, comprising capturing a series of images of a user in a car by a camera in the car, wherein each image comprises one or more colour signals; for each of the images: locating a face of the user in the image; determining a boundary in the image, wherein the face is located within the boundary; detecting one or more facial features within the boundary; and based on the detected facial features, determining one or more regions in the image representing skin patches in the face; analysing the colour signals in the regions representing the skin patches; and determining one or more heart beat features based on the analysis. The method further comprising selecting one or more pulse waves and/or frequency spectra of one or more skin patches reaching a predeter- (Continued)

200
202 Extracting colour change
204 Associating colour change with blood flow intensity
206 Creating pulse wave
208 Splitting pulse wave into overlapping time windows
210 Transforming each window into frequency space
212 Summing up window spectra
214 Creating frequency spectra
216 Comparing spectra with ideal pulse wave pattern
218 If < similarity threshold
220 Discarding pulse wave
222 If > similarity threshold
224 Forming weighted pulse average
226 Detecting noise level
228 If > noise threshold
230 Discarding
232 If < noise threshold
300 To Fig. 3 mined level of similarity and/or a predetermined level of noise for further analysis and discarding all other pulse waves and/or frequency spectra. The method improves speed and accuracy of determining one or more heart beat features using rPPG.

8 Claims, 3 Drawing Sheets

(56) References Cited

U.S. PATENT DOCUMENTS

| | | | | |
|---|---|---|---|---|
| 2012/0203077 | A1* | 8/2012 | He | A61B 5/02055 600/382 |
| 2017/0238842 | A1 | 8/2017 | Jacquel et al. | |
| 2019/0307365 | A1 | 10/2019 | Addison et al. | |
| 2019/0350471 | A1 | 11/2019 | Marks et al. | |
| 2022/0110534 | A1* | 4/2022 | Okubo | A61B 5/1176 |

FOREIGN PATENT DOCUMENTS

| | | | | |
|---|---|---|---|---|
| JP | 2015205050 | A | 11/2015 | |
| JP | 2017153773 | A | 9/2017 | |
| JP | 2017158675 | A | 9/2017 | |
| JP | 2018068720 | A | 5/2018 | |
| JP | 2018164587 | A | 10/2018 | |
| JP | 2020527088 | A | 9/2020 | |
| JP | 2020178964 | A | 11/2020 | |
| KR | 101738278 | B1 | 5/2017 | |
| KR | 20200061016 | A | 6/2020 | |
| WO | 2016158624 | A1 | 10/2016 | |
| WO | WO-2020153194 | A1 * | 7/2020 | A61B 5/4845 |

OTHER PUBLICATIONS

Xiong, X. et al., "Supervised Descent Method and Its Applications to Face Alignment," Proceedings of the 2013 IEEE Conference on Computer Vision and Pattern Recognition, Jun. 23, 2013, Portland, Oregon, 8 pages.

Kumar, M. et al., "DistancePPG: Robust non-contact vital signs monitoring using a camera," Biomedical Optics Express, vol. 6, No. 5, May 1, 2015, 24 pages.

Lam, A. et al., "Robust Heart Rate Measurement from Video Using Select Random Patches," Proceedings of the 2015 IEEE International Conference on Computer Vision (ICCV), Dec. 7, 2015, Santiago, Chile, 9 pages.

Hassan, F. et al., "Closed loop blood glucose control in diabetics.," Biomedical Research, vol. 28, No. 16, 2017, 7 pages.

Po, L. et al., "Block-based adaptive ROI for remote photoplethysmography," Multimedia Tools and Applications, vol. 77, No. 1, Mar. 13, 2017, 27 pages.

Hartford, M. et al., "Availability and performance of image-based, non-contact methods of monitoring heart rate, blood pressure, respiratory rate, and oxygen saturation: a systematic review," Physiological Measurement, vol. 40, No. 6, Jun. 2019, 18 pages.

Gudi, A. et al., "Efficient Real-Time Camera Based Estimation of Heart Rate and Its Variability," arXiv Cornell University Website, Available Online at https://arxiv.org/abs/1909.01206, Sep. 3, 2019, 10 pages.

Nasrullah, M. et al., "Vision-Based Heart and Breath Rate Monitoring Using Skin Color and Motion," Proceedings of the 2019 International Electronics Symposium (IES), Sep. 27, 2019, Surabaya, Indonesia, 6 pages.

Wang, W. et al., "Discriminative Signatures for Remote-PPG," IEEE Transactions on Bio-Medical Engineering, vol. 67, No. 5, May 2020, Available Online Aug. 30, 2019, 12 pages.

Gudi, A. et al., "Real-time Webcam Heart-Rate and Variability Estimation with Clean Ground Truth for Evaluation," arXiv Cornell University Website, Available Online at https://arxiv.org/abs/2012.15846, Available as Early as Dec. 31, 2020, 22 pages.

Liu, S. et al., "Multi-Channel Remote Photoplethysmography Correspondence Feature for 3D Mask Face Presentation Attack Detection," IEEE Transactions on Information Forensics and Security, vol. 16, Jun. 8, 2021, 14 pages.

ISA European Patent Office, International Search Report and Written Opinion Issued in Application No. PCT/RU2021/000135, Dec. 23, 2021, WIPO, 22 pages.

Japanese Patent Office, Office Action Issued in Application No. 2023-555268, May 19, 2025, 9 pages.

Korea Intellectual Property Office, Office Action Issued in Application No. 10-2023-7032110, Oct. 27, 2025, 14 pages. (Submitted with English Translation).

* cited by examiner

400

402

Camera

404

Computer device

METHOD AND SYSTEM FOR HEART RATE EXTRACTION FROM RGB IMAGES

CROSS-REFERENCE TO RELATED APPLICATIONS

The present application is a U.S. National Phase of International Application No. PCT/RU2021/000135, entitled "METHOD AND SYSTEM FOR HEART RATE EXTRACTION FROM RGB IMAGES", and filed on Mar. 30, 2021. The entire contents of the above-listed application are hereby incorporated by reference for all purposes.

FIELD

The present disclosure relates to methods and systems for monitoring a physiological or psychological condition of a person, in particular to determining heart beat features, such as heart rate and inter-beat intervals.

BACKGROUND

Heart beat features are a source of human physiological and psychological information. Parameters like heart rate itself, heart inter-beat intervals and its variability are essential to monitor a person's health and wellbeing. Contact heart rate measurement devices and sensors, such as pulsometers, ECG devices or PPG devices like smartwatches and wristbands, are widespread. There are also contactless devices available exploiting RGB cameras or radars as sensors (Harford et al., Physiol. Measurements, 40(6), 2019). The methodology using RGB cameras to measure heart rate is called rPPG—remote photoplethysmography (Hassan et al., Biomed. Sign. Proc. And Control, 2017; Lam and Kuno, Robust heart rate measurement from video using select random patches, ICCV-IEEE 2015). The method exploits the fact that skin slightly changes its colour following blood pulses. Contactless technologies are more appropriate for applications in e.g. in-cabin car monitoring systems. As modern cars are no longer just a means of commuting, but act as a living space, cars are integrated with more and more features and functions, sometimes not directly related to driving, e.g. for monitoring driver's and occupant's physiological state and health. This issue is of particular importance as cognitive load and stress, as well as (non-visual) distraction are known to strongly influence driving performance.

The following publications relate to the technological background of the present disclosure:

U.S. Pat. No. 9,642,536B2 deals with the analysis of a video of one or more people. Heart rate information is determined from the video and the heart rate information is used in mental state analysis. The heart rate information and resulting mental state analysis are correlated to stimuli, such as digital media which is consumed or with which a person interacts. The heart rate information is used to infer mental states. The mental state analysis, based on the heart rate information, can be used to optimize digital media or modify a digital game.

U.S. Pat. No. 8,977,347B2 discloses an rPPG method and system for estimating heart rate variability from time-series signals generated from video images captured of a subject of interest being monitored for cardiac function. Low frequency and high frequency components are extracted from a time-series signal obtained by processing a video of the subject being monitored. A ratio of the low and high frequency of the integrated power spectrum within these components is computed. Analysis of the dynamics of this ratio over time is used to estimate heart rate variability. The teachings hereof can be used in a continuous monitoring mode with a relatively high degree of measurement accuracy and find their uses in a variety of diverse applications such as, for instance, emergency rooms, cardiac intensive care units, neonatal intensive care units, and various telemedicine applications.

Known rPPG methods, however, lack accuracy and speed in determining the driver's or occupant's head position and identifying face structures for further image evaluation. Further, known rPPG analyses suffer from poor signal-to-noise ratios leading to inaccurate heart feature detection. Therefore, a need exists for a blood flow measurement technique which is configured for optimized skin patch location and analysis at high speed and high accuracy.

SUMMARY

A first aspect of the present disclosure relates to a method for determining one or more heart beat features. The method comprises:

- capturing a series of images of a user in a car by a camera in the car, wherein each image comprises one or more colour signals;

for each of the images:

- locating a face of the user in the image;
- determining a boundary in the image, wherein the face is located within the boundary;
- detecting one or more facial features within the boundary; and
- based on the detected facial features, determining one or more regions in the image representing skin patches in the face;
- analysing the colour signals in the regions representing the skin patches; and determining one or more heart beat features based on the analysis.

The objective of the method is to determine heart beat features by remote photoplethysmography (rPPG), based on an image series of the skin patches of the user's face. The method may be conducted in a vehicle such as a car allowing determining the heart rate or other heat beat features of a driver or a passenger of a vehicle. Thereby, the health of the user can be monitored when driving, without the user unduly investing time into health monitoring. Monitoring the health of a driver allows, for example, for generating an output signal to invite the driver to stop the car in case of acute health problems.

According to the present disclosure, determining one or more skin patches of the face of the user comprises locating the face of the user in the image and determining a boundary in the image, which is framing the face. Facial features, such as, eyebrows, eyes, nose or mouth, are detected within this boundary. The advantage of narrowing the search area of facial features to within this boundary is that only the relevant image section is analysed. Therefore, the detection of facial features becomes faster. The facial features are used to determine the location of the skin patches in the face.

In an embodiment, the capturing of a series of images is preferably performed using a visual light camera capturing RGB images. This enables the selection of the colour component with the biggest dynamic range for further analysis of the RGB image series.

In a further embodiment, analysing the colour signals further comprises extracting colour changes in the series of images of one or more skin patches in order to determine temporal fluctuations of the colour at different position within the face. Data collection at different positions allows for optional subsequent selection of most suitable images. To improve data accessibility for further digital analysis, colour changes are translated into a sequence of numerical values creating a pulse wave for each skin patch based on the colour changes.

In an embodiment, the method further comprises determining blood flow intensities based on the colour changes. The image sequences and temporal fluctuations of colours are thereby connected to blood flow fluctuations through blood vessels of the skin induced by the heart beat. This correlation enables signal analysis and interpretation.

The method further comprises transforming each of the pulse waves of each of the skin patches into a frequency space to generate frequency spectra for each of the skin patches. This facilitates further digital image processing and allows summing up all spectra of one skin patch.

In an alternative embodiment, generating frequency spectra further comprises:

splitting the pulse waves from each skin patch into one or more overlapping time windows;

transforming each of the windows into the frequency space to generate frequency spectra;

summing up said spectra into one accumulated spectrum.

It is beneficial for data analysis to form overlapping windows, transform each window individually into the frequency space and then sum up all spectra, because thereby frequency components belonging to noise can be eliminated.

Further, in some embodiments, each frequency spectrum is compared with a predetermined pulse wave pattern and a level of similarity is determined. The level of similarity between the frequency spectra and the predetermined wave pattern acts as a quality measure. If, for example, pulse waves do not reach a predetermined threshold, i.e. a predetermined level of similarity with the predetermined pulse wave pattern, all such pulse waves are discarded. Consequently, noisy frequency spectra and corresponding skin patches are eliminated from further analysis. However, all pulse waves, for which the predetermined similarity level is reached, are summed up and a weighted average is determined. The weights correspond to the similarity, i.e. the higher the similarity of a particular pulse wave to the predetermined wave, the bigger its contribution to the sum. Thus, such an algorithm may select skin patches that are particularly suitable for determining heart beat features using rPPG analysis, rendering the analysis more accurate.

In an embodiment, the method further comprises detecting a noise level of each weight-averaged spectrum and summing up all pulse waves for which the noise level does not exceed a predetermined threshold to an accumulated pulse wave. This additional selection of pulse waves with the best signal-to-noise ratio results in the formation of an accumulated pulse wave with decreased noise.

According to the rPPG method, in an embodiment the method further comprises processing any of the above pulse waves to extract heart rate features, wherein the heart rate features comprise one or more of heart rate, inter-beat intervals and heart rate variability. Therefore, in particular, peaks of the pulse wave functions are identified to determine inter-beat intervals or heart rates. Spectrum analysis may be further performed to determine heart rate variability.

The method may further comprise the heart rate features being classified into a plurality of classes, wherein the classes are associated with different psychological and/or physiological states of the user. For this, heart rate features are interpreted based on medical studies and act as sources of information about human inner states such as, but not limited to, high cognitive load, stress or drowsiness. This information may be used to monitor health and wellbeing.

According to a second aspect of the disclosure, a system for determining one or more heart beat features is provided. The system comprises a camera and a computing device. The system is configured to execute the steps described above. All properties of the method of the present disclosure also apply to the system.

BRIEF DESCRIPTION OF THE DRAWINGS

The features, objects, and advantages of the present disclosure will become more apparent from the detailed description set forth below when taken in conjunction with the drawings in which like reference numerals refer to similar elements.

DETAILED DESCRIPTION OF THE PREFERRED EMBODIMENTS

Figure 1:
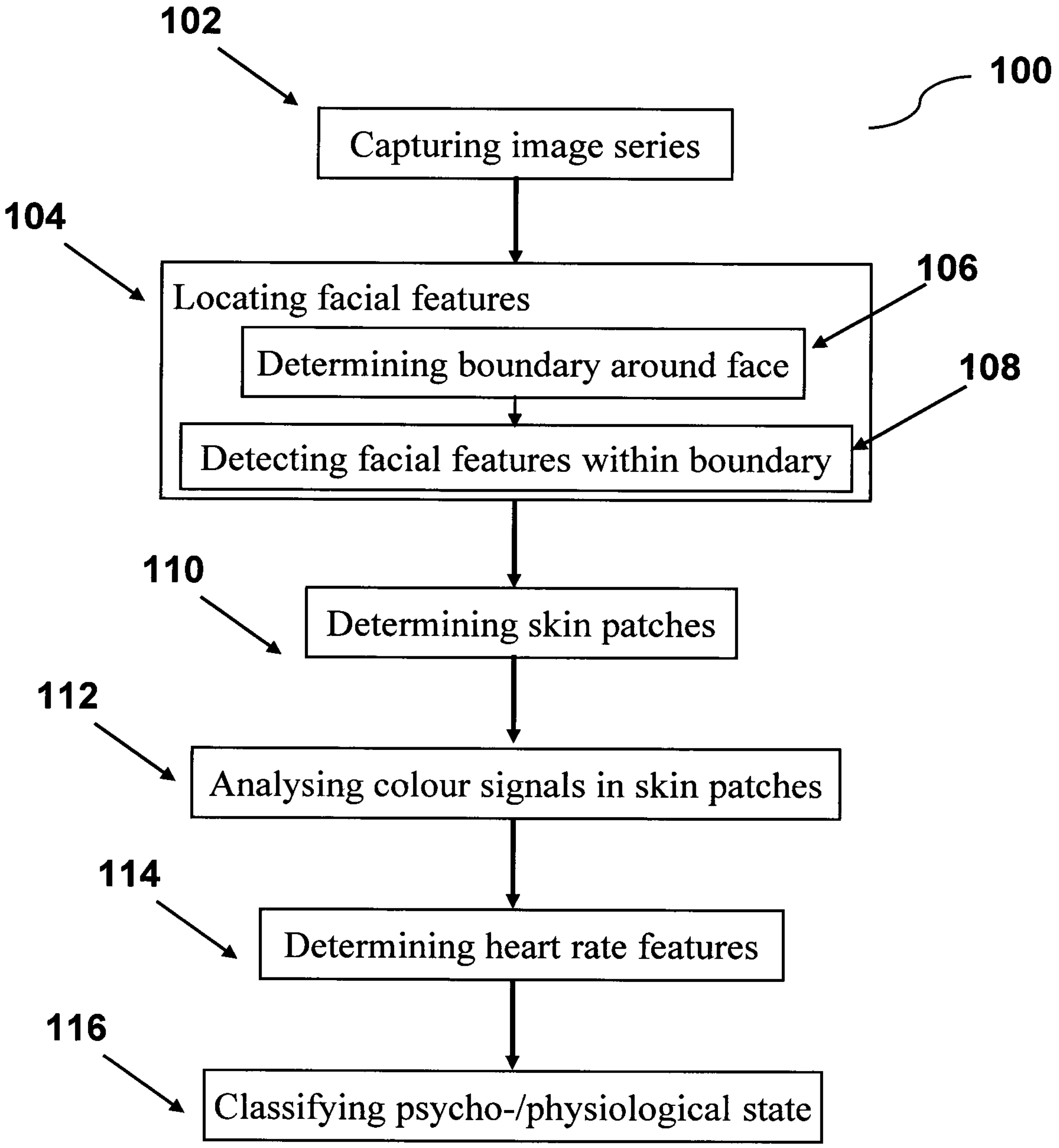
FIG. 1 depicts a flow chart of a method 100 for determining one or more heart beat features according to one or more embodiments.

FIG. 1 depicts a flow chart of a method 100 for determining one or more heart beat features according to an embodiment. The method comprises capturing a series of images 102 of the face of a user in a car. In a preferred embodiment, the images are RGB images captured by a visual light camera. The sequence of images may be generated at a typical frame rate of e.g. 30 frames per second. Each frame represents a set of pixels. Each pixel can be monochromatic or contain a range of wavelengths, such as a red, a green and a blue component in RGB images. Using RGB images and thus capturing three colour components allows selecting the colour component with the biggest dynamic range over the series of images for further analysis.

The method further comprises locating facial features 104 of the user in one or more images 102. Locating the facial features 104 may be split into two phases. The first phase may comprise locating the face of the user in the image and determining a boundary in the image, which is framing the face 106. This first phase may be a coarse location of the face of the user and a boundary may be a rectangular frame bounding the face. The second phase comprises detecting facial features, such as, eyebrows, eyes, nose or mouth, within this boundary 108. Narrowing the search areas to within this boundary allows for a faster and more accurate detection of facial features.

The facial features are key points for understanding the face structure and determining specific skin patches 110, i.e. pixels belonging to the face skin of the user. The skin patches may vary in size, homogeneity, face structure and head position.

The method further comprises analysing colour signals of one or more skin patches 112. Analysing colour signals of the skin patches comprises extracting colour changes in the series of images of the face of the user at one or more positions of the face of the user. Data collection at different positions allows for optional subsequent selection of most suitable skin patches for further data analysis. The temporal fluctuations of the colour may be translated into a sequence of numerical values, i.e. a pulse wave, for improved data accessibility in further analysis. Analysing colour signals may be performed in accordance with the flow chart of FIG. 2.

In rPPG, colour changes in form of periodic pulse waves relate to blood flow fluctuations through the blood vessels of the skin. This correlation enables signal analysis and interpretation.

The method further comprises determining heart rate features 114, such as but not limited to, heart rate, inter-beat intervals and heart rate variability, from the pulse waves. This may include detecting peaks in the pulse waves, determining peak distances and determining heart beat or inter-beat intervals based on the pulse waver pattern. Other types of pulse wave analyses may be applied to determine for example heart rate variability.

The method further comprises classifying a psychological and/or physiological state 116 of the user into a plurality of classes, wherein the classes are associated with different psychological and/or physiological states of the user. For this, heart rate features may be interpreted based on medical studies and may act as sources of information about inner states like high cognitive load, stress, drowsiness, and many others. This information may be used to monitor health and wellbeing, to predict and pre-diagnose diseases such as depression or sleep disorders and to detect diseases such as epilepsy, panic attacks, heart attacks and many more.

Figure 2:
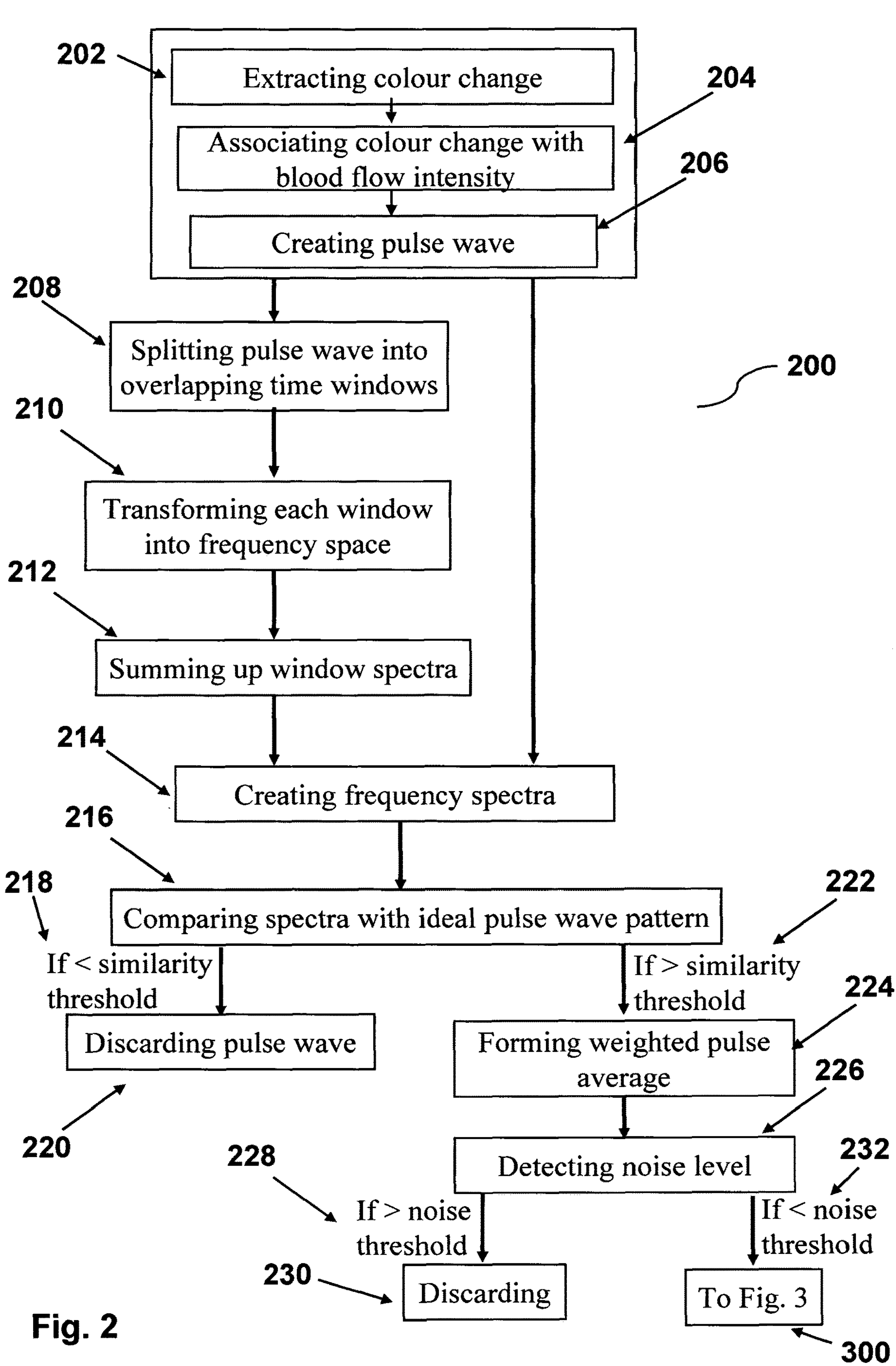
FIG. 2 depicts a flow chart of a method 200 for analysing image data according to one or more embodiments.

FIG. 2 depicts a flow chart of a method 200 for analysing image information according to an embodiment. Analysing colour signals 112 in each of the skin patches of the face of the user or colour signals in any image of the face of the user and translating the colour changes in the series of images into a pulse wave may comprise further digital data processing and data selection in order to enable more accurate determination of heart rate features. The method comprises extracting colour changes 202 in the series of images. In a preferred embodiment, the images may be RGB images and the colour component with the biggest dynamic range may be selected.

The method further comprises associating colour changes with blood flow intensities 204. The colour changes may be periodical and correspond to heart rate features.

The method comprises translating such colour changes into a sequence of numerical values and creating a pulse wave 206.

The method may further comprise transforming each of the pulse waves of each of the skin patches into a frequency space to generate frequency spectra 214 for each of the skin patches. This facilitates further digital image processing and allows summing up all spectra of one skin patch.

In an alternative embodiment, creating frequency spectra 214 can further comprise: splitting the pulse waves from each skin patch into one or more overlapping time windows 208; transforming each of the windows into the frequency space to generate frequency spectra 210; and summing up said spectra into one accumulated spectrum 212. Forming overlapping windows, transforming each window individually into the frequency space and summing up all spectra allows eliminating frequency components belonging to noise.

Further, in some embodiments, the method comprises comparing each frequency spectrum with a predetermined pulse wave pattern 216 and determining a level of similarity between each frequency spectrum and/or each pulse wave and the predetermined pulse wave. The predetermined pulse wave pattern may resemble an ideal wave and may correlate directly to blood flow intensities. The level of similarity between the frequency spectra and/or pulse wave and the predetermined wave pattern may act as a quality measure. If, for example, pulse waves do not reach a predetermined threshold 218, i.e. a predetermined level of similarity with the predetermined pulse wave pattern, the method comprises discarding all such pulse waves 220. Consequently, noisy frequency spectra and corresponding skin patches are eliminated from further analysis. The method further comprises forming a weighted pulse wave average 224 from all pulse waves, for which the predetermined similarity level is reached 222. The weights of the individual pulse waves contributing to the weighted average pulse wave correspond to the similarity, i.e. the higher the similarity of a particular pulse wave to the predetermined wave, the bigger its contribution to the sum. Thus, such an algorithm may select skin patches that are particularly suitable for determining heart beat features using rPPG analysis and thereby improve the accuracy of determining heart rate features.

In an embodiment, the method may further comprise detecting a noise level 226 of each weight-averaged spectrum and summing up all pulse waves for which the noise level does not exceed a predetermined threshold 232 to an accumulated pulse wave 300. The method comprises discarding all pulse waves 230 for which a predetermined noise threshold is exceeded 228. This additional selection of pulse waves with the best signal-to-noise ratio results in the formation of a corrected pulse wave with decreased noise level.

Figures 3, 4:
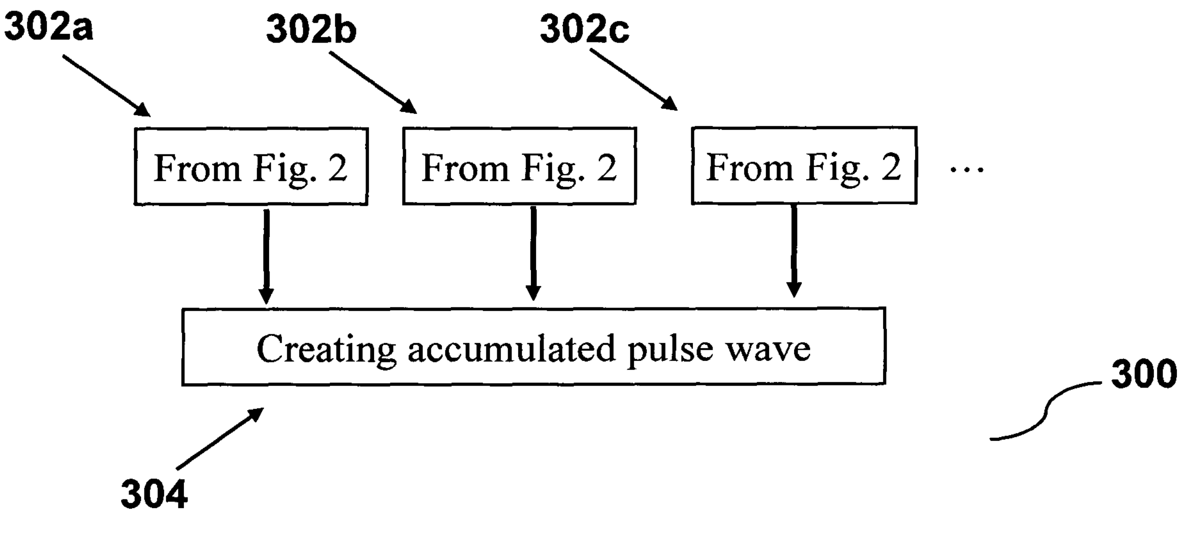
FIG. 3 depicts a flow chart of a method 300 for determining image data according to one or more embodiments.
FIG. 4 depicts a block diagram of a system 400 for determining one or more heart beat features.

FIG. 3 depicts a flow chart of a method 300 for determining image information according to another embodiment. In an embodiment, the creation of a pulse wave used for heart rate feature extraction may comprise analysing image information according to method 200 for each of the skin patches in the face of the user and select the suitable pulse waves with the best signal-to-noise ratio for each of the skin patches 302*a*, 302*b*, 302*c*, . . . for further analysis. The method may further comprise summing up or determining an average of the corrected pulse waves 302*a*, 302*b*, 302*c*, . . . with decreased noise level and creating an accumulated pulse wave 304, which may contain a minimum of noise and may be used for determining heart rate features with high accuracy.

FIG. 4 depicts a block diagram of a system 400 for determining one or more heart beat features according to an embodiment. The system comprises a camera 404 and a computer device 406. In a preferable embodiment, the camera 404 is a visible light camera. The camera faces the user of the system, and records a series of images of the user's face. The camera may have a horizontal field of view of 180-200°. Typical frame rates for the camera may be e.g. between 30 frames per second (fps) and 60 fps. The camera resolution for the camera is high enough to allow recognizing facial contours and features, such as the locations of eyes, eyebrows, nose, and mouth. A typical value may be 1920 px×1080 px, for example. The system is configured to execute the methods described above.

REFERENCE SIGNS

100 Method for determining one or more heart beat features
102-116 Steps of method 100
200 Method for analysing image data
202-232 Steps of method 200
300 Method for determining image data

302-304 Steps of method 300

400 System for determining one or more heart beat features

402 Camera

404 Computer device

The invention claimed is:

1. A method for determining one or more heart beat features, the method comprising:

capturing a series of images of a user in a car by a camera in the car, wherein each image comprises one or more colour signals;

for each of the images:

locating a face of the user in the image;

determining a boundary in the image, wherein the face is located within the boundary;

detecting one or more facial features within the boundary; and based on the detected facial features, determining one or more regions in the image representing skin patches in the face;

analysing the colour signals in the regions representing the skin patches; and determining one or more heart beat features based on the analysis;

wherein analysing the colour signals further comprises:

determining colour changes in the series of images of one or more skin patches;

creating a pulse wave for each skin patch based on the colour changes;

splitting the pulse waves from each skin patch into a plurality of overlapping time windows, wherein each of the plurality of overlapping time windows overlaps in time with an adjacent time window of the plurality of time windows;

transforming each of the windows into the frequency space to generate frequency spectra;

summing up said spectra into one accumulated spectrum;

comparing each frequency spectrum with a predetermined pulse wave pattern and determining a level of similarity;

discarding all pulse waves for which the level of similarity does not reach a first predetermined threshold; and determining a weighted average of all pulse waves for which the level of similarity does reach the first predetermined threshold, wherein the level of similarity defines weights for the weighted average.

2. The method of claim 1, wherein capturing a series of images is performed using a visual light camera capturing RGB images.

3. The method of claim 1, further comprising determining blood flow intensities based on the colour changes.

4. The method of claim 1, further comprising detecting a noise level of each weight-averaged spectrum; and summing up all pulse waves for which the noise level does not exceed a predetermined threshold to an accumulated pulse wave.

5. The method of claim 1, further comprising processing the pulse wave to extract heart rate features, wherein the heart rate features comprise one or more of heart rate, inter-beat intervals and heart rate variability.

6. A system for determining one or more heart beat features, the system comprising:

a camera; and a computing device;

wherein the system is configured to execute the method of claim 1.

7. The system of claim 6, wherein the camera is a visible light camera capturing RGB images.

8. The method of claim 4, further comprising discarding all pulse waves for which the noise level exceeds a second predetermined threshold.

* * * * *